United States Patent
Kao et al.

(10) Patent No.: US 11,739,050 B2
(45) Date of Patent: Aug. 29, 2023

(54) METHOD FOR PURIFICATION OF TERPENOID AMINO ALCOHOL DERIVATIVES

(71) Applicant: SCI PHARMTECH INC., Taoyuan (TW)

(72) Inventors: Chen-Yi Kao, Taoyuan (TW); Feng-Hsu Li, Taoyuan (TW)

(73) Assignee: SCI PHARMTECH INC., Taoyuan (TW)

( * ) Notice: Subject to any disclaimer, the term of this patent is extended or adjusted under 35 U.S.C. 154(b) by 31 days.

(21) Appl. No.: 17/467,974

(22) Filed: Sep. 7, 2021

(65) Prior Publication Data

US 2023/0103071 A1    Mar. 30, 2023

(51) Int. Cl.
C07C 213/10 (2006.01)
C07C 213/02 (2006.01)
C07D 301/03 (2006.01)

(52) U.S. Cl.
CPC .......... *C07C 213/10* (2013.01); *C07C 213/02* (2013.01); *C07D 301/03* (2013.01); C07C 2601/14 (2017.05)

(58) Field of Classification Search
CPC .................................................. C07C 213/10
See application file for complete search history.

(56) References Cited

PUBLICATIONS

Said, L. Ait., et al. "Kinetic Separation of cis- and trans-Limonene Epoxide: Reaction of Diastereomeric Mixture of Limonene Oxides with Secondary Amine and Carbamate." Asian J. of Chemistry. (2021), vol. 33, No. 11, pp. 2667-2670. (Year: 2021).*

* cited by examiner

*Primary Examiner* — John S Kenyon
(74) *Attorney, Agent, or Firm* — Osha Bergman Watanabe & Burton LLP

(57) ABSTRACT

Provided is a method of purifying a terpenoid amino alcohol derivative, including providing a crude terpenoid amino alcohol derivative; performing an acid/base crystallization process of the crude terpenoid amino alcohol derivative to obtain an organic salt; and reacting the organic salt with NaOH and toluene to obtain a purified terpenoid amino alcohol derivative. Also provided is a method of preparing p-mentha-2,8-diene-1-ol from the purified terpenoid amino alcohol derivative.

20 Claims, 1 Drawing Sheet

METHOD FOR PURIFICATION OF TERPENOID AMINO ALCOHOL DERIVATIVES

BACKGROUND

1. Technical Field

The present disclosure relates to methods of purifying terpenoid amino alcohol derivatives, and to methods of preparing p-mentha-2,8-diene-1-ol from the terpenoid amino alcohol derivatives.

2. Description of Associated Art (+)-p-mentha-2,8-diene-1-ol is an intermediate for preparation of cannabidiol, which has several therapeutic applications, e.g., for serving as an anti-arthritic agent or a neuroprotective antioxidant (Proc. Natl. Acad. Sci. U.S.A. 2000, 97, 9561 and Proc. Natl. Acad. Sci. U.S.A. 1998, 95, 8268).

(+)-p-mentha-2,8-diene-1-ol was originally synthesized from (+)-limonene with one step through $O_2$-sensitized photoreaction, but its target compound is difficult to be isolated from the reaction mixture that results in poor yield (Justus Liebigs Ann. Chem. 1964, 674, 93). In addition, several approaches have reported chemical synthesis of (+)-p-mentha-2,8-diene-1-ol from (+)-limonene. For example, as shown in Scheme 1 below, a process containing the steps of (A) oxidation of an endocyclic moiety for forming epoxy derivatives, (B) ring opening with nucleophiles, and (C) oxidation and elimination reactions has been disclosed to obtain (+)-p-mentha-2,8-diene-1-ol (U.S. Pat. No. 4,433,183; Aust. J. Chem., 1980, 33, 451; and Tetrahedron Letters 2013, 54, 52-54).

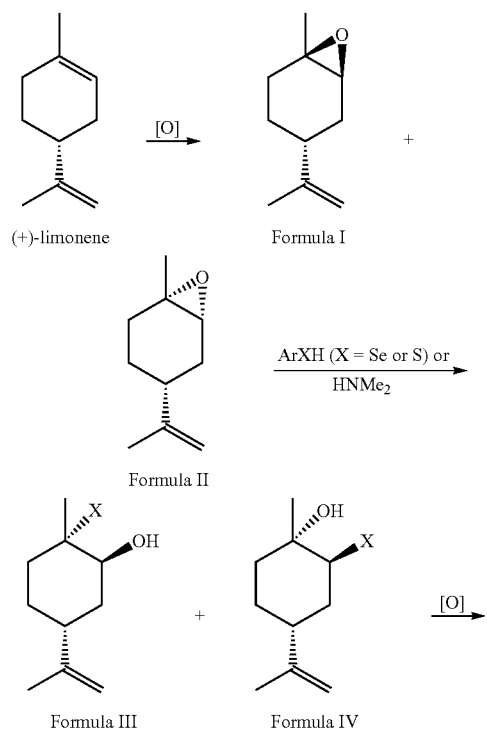

Scheme 1. Synthesis of (+)-p-mentha-2,8-diene-1-ol

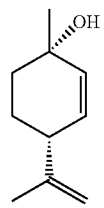

(+)-p-mentha-2,8-diene-1-ol

Specifically, 1:1 diastereomer mixture (formula I and formula II) is obtained by epoxidation of (+)-limonene (i.e., step A). Such reaction mixture directly undergoes an epoxide ring opening reaction (i.e., step B) to perform regio- and stereo-selectivity and obtain about 40% yield of tertiary alcohol (formula IV), unreacted cis-isomer (formula I) and a trace amount of secondary alcohol (formula III). For the following oxidation reaction (i.e., step C), a purification process is suggested by utilizing distillation if X is phenyl sulfide (SPh), or is not necessary if X is phenyl selenide (SePh) or $NMe_2$ (Me: methyl). However, both of these two conditions inevitably cause energy waste and low reaction efficiency.

Accordingly, an efficient, economical and safe purification process of intermediates is still needed for preparation of (+)-p-mentha-2,8-diene-1-ol.

SUMMARY

In view of the foregoing, the present disclosure provides a method of purifying an intermediate for preparation of p-mentha-2,8-diene-1-ol. In at least one embodiment of the present disclosure, a method of purifying a terpenoid amino alcohol derivative represented by formula V' below is provided:

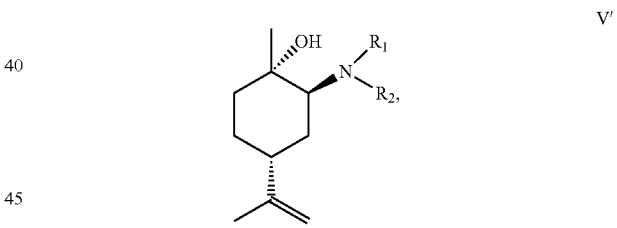

wherein $R_1$ and $R_2$ are independently a substituted or unsubstituted C1-C6 alkyl.

In at least one embodiment of the present disclosure, the method comprises: providing a crude terpenoid amino alcohol derivative represented by formula V' above; performing an acid/base crystallization process of the crude terpenoid amino alcohol derivative represented by formula V' to obtain an organic salt represented by formula V''' below:

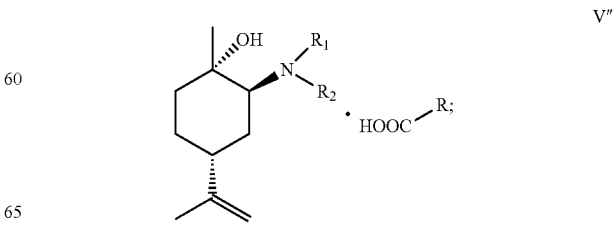

and reacting the organic salt represented by formula V″ with at least one solvent selected from NaOH, toluene, cyclopentyl methyl ether (CPME), diethyl ether, and dimethoxyethane (DME) to obtain a purified terpenoid amino alcohol derivative represented by formula V′, wherein R is independently a substituted or unsubstituted C1-C6 alkyl.

In at least one embodiment of the present disclosure, the terpenoid amino alcohol derivative may be represented by formula V below:

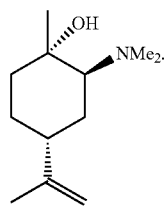

V

In some embodiments, the organic salt may be represented by formula VI or VII below:

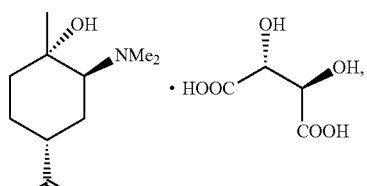

VI

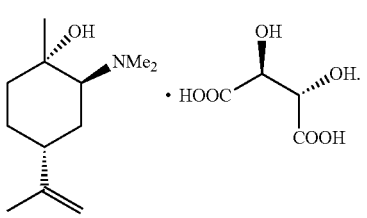

VII

In at least one embodiment of the present disclosure, the acid/base crystallization process is performed by mixing the crude terpenoid amino alcohol derivative as a base with an organic acid in an organic solvent or an organic/aqueous solution.

In at least one embodiment of the present disclosure, in the acid/base crystallization process, the organic acid may be L-tartaric acid, D-tartaric acid, acetic acid (HOAc), citric acid, camphorsulfonic acid, mandelic acid, (+)-di-tert-butyl tartaric acid, (+)-diethyl tartaric acid, methanesulfonic acid, or a combination thereof. In some embodiments of the present disclosure, the organic acid is L-tartaric acid, D-tartaric acid, or a combination thereof.

In at least one embodiment of the present disclosure, in the acid/base crystallization process, the ratio of the organic acid to the base in the mixture is 1:1 to 1:3. In some embodiments of the present disclosure, the ratio of the organic acid to the base in the mixture may be 1:1.

In at least one embodiment of the present disclosure, in the acid/base crystallization process, the organic solvent may be isopropyl alcohol, and the organic/aqueous solution may be acetone/$H_2O$ solution.

In at least one embodiment of the present disclosure, the acid/base crystallization process is performed at a temperature ranging from −5° C. to 30° C. In some embodiments of the present disclosure, the acid/base crystallization process may be performed at a temperature ranging from 5° C. to 15° C., such as about 6° C., about 7° C., about 8° C., about 9° C., about 10° C., about 11° C., about 12° C., about 13° C., and about 14° C. In at least one embodiment of the present disclosure, the acid/base crystallization process is performed at a temperature about 10° C.

In at least one embodiment of the present disclosure, the method further comprises stripping the purified terpenoid amino alcohol derivative with isopropyl alcohol or acetone/$H_2O$ solution, thereby obtaining the solid terpenoid amino alcohol derivative.

In at least one embodiment of the present disclosure, a method of preparing p-mentha-2,8-diene-1-ol is also provided, and the method of preparing p-mentha-2,8-diene-1-ol comprises: purifying a terpenoid amino alcohol derivative represented by formula V′ by the purification method as mentioned above; oxidizing the purified terpenoid amino alcohol derivative represented by formula V′ with $H_2O_2$ to form a reaction mixture; and performing a Cope elimination of the reaction mixture to obtain p-mentha-2,8-diene-1-ol.

In at least one embodiment of the present disclosure, the oxidization of the purified terpenoid amino alcohol derivative may be performed in isopropyl alcohol or acetone/$H_2O$ solution at a temperature ranging from 50° C. to 70° C.

In at least one embodiment of the present disclosure, the method of preparing p-mentha-2,8-diene-1-ol further comprises quenching the oxidization with $Na_2SO_3$ and $H_2O$, and then distilling the reaction mixture after the Cope elimination.

In at least one embodiment of the present disclosure, the method of preparing p-mentha-2,8-diene-1-ol further comprises providing a mixture comprising intermediates represented by formulas I and II below:

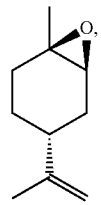

I

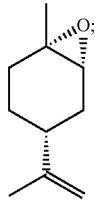

II and reacting the mixture with dimethylamine in an alcohol to obtain the terpenoid amino alcohol derivative represented by formula V′ for the purification process.

In at least one embodiment of the present disclosure, the reaction of the mixture may be performed at a temperature ranging from 50° C. to 60° C.

In at least one embodiment of the present disclosure, the alcohol for reacting the mixture may be an alcohol having a lower carbon number, such as methanol (MeOH).

In at least one embodiment of the present disclosure, the method of preparing p-mentha-2,8-diene-1-ol further comprises performing an epoxidation of limonene to provide the mixture.

In the present disclosure, efficient methods are provided to obtain high purity of an intermediate for further preparing p-mentha-2,8-diene-1-ol. In accordance with the embodiments of the present disclosure, the intermediate represented by formula V' can be easily purified and isolated without using an energy-costly distillation process or an unpurified reactant for an ongoing process. Therefore, the methods of the present disclosure are useful in improving efficiency of preparation of p-mentha-2,8-diene-1-ol.

BRIEF DESCRIPTION OF THE DRAWINGS

The present disclosure can be more fully understood by reading the following descriptions of the embodiments, with reference made to the accompanying drawings.

DETAILED DESCRIPTION OF THE EMBODIMENTS

Figure 1:
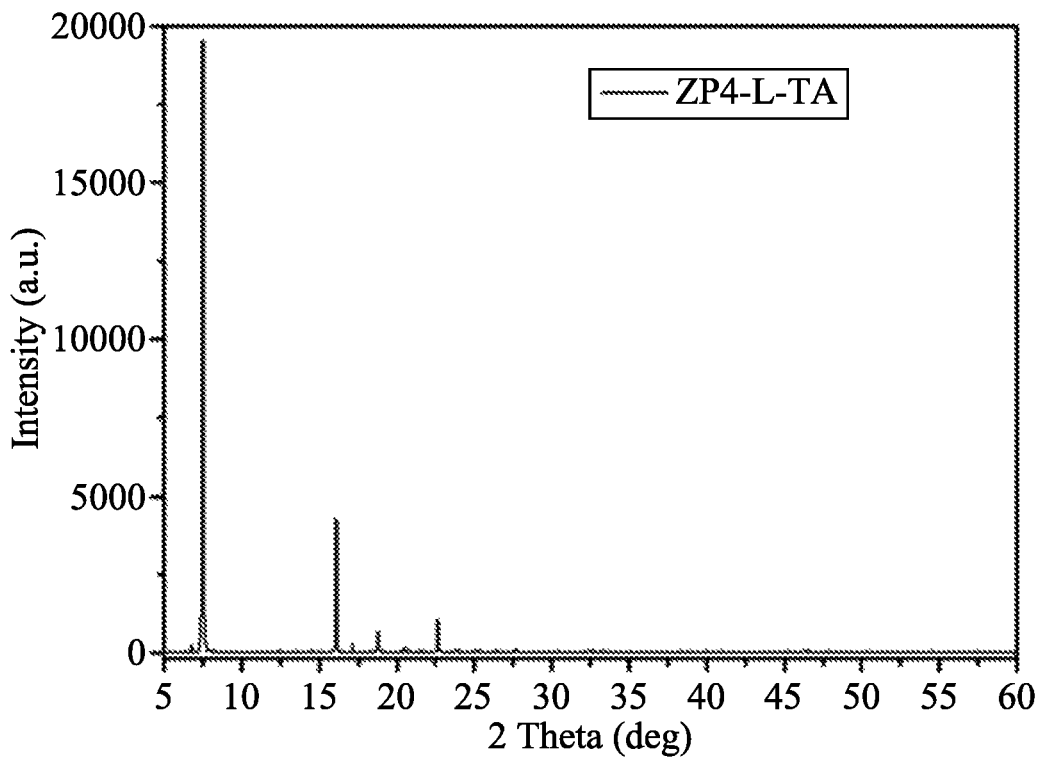
FIG. 1 illustrates the powder x-ray diffraction pattern of an organic salt represented by formula VI.

The following examples are used for illustrating the present disclosure. A person skilled in the art can easily conceive the other advantages and effects of the present disclosure, based on the disclosure of the specification. The present disclosure can also be implemented or applied as described in different examples. It is possible to modify or alter the examples for carrying out this disclosure without contravening its scope, for different aspects and applications.

It is further noted that, as used in this specification, the singular forms "a," "an," and "the" include plural referents unless expressly and unequivocally limited to one referent. The term "or" is used interchangeably with the term "and/or" unless the context clearly indicates otherwise.

The present disclosure is directed to a method of purifying an intermediate for preparation of p-mentha-2,8-diene-1-ol. In at least one embodiment of the present disclosure, the intermediate for preparation of p-mentha-2,8-diene-1-ol is a terpenoid amino alcohol derivative represented by formula V' below:

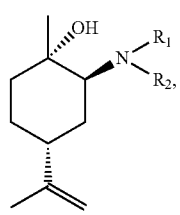

V' wherein $R_1$ and $R_2$ are independently a substituted or unsubstituted C1-C6 alkyl.

In at least one embodiment of the present disclosure, $R_1$ and $R_2$ in formula V' may be independently methyl, ethyl, n-propyl, n-butyl, isobutyl, or sec-butyl. In another embodiment of the present disclosure, the terpenoid amino alcohol derivative is represented by formula V below:

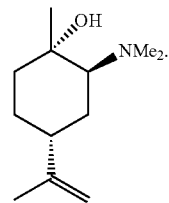

V

In at least one embodiment of the present disclosure, the method of purifying the terpenoid amino alcohol derivative comprises providing a crude terpenoid amino alcohol derivative; performing an acid/base crystallization process of the crude terpenoid amino alcohol derivative to obtain an organic salt; and reacting the organic salt with at least one solvent selected from NaOH, toluene, CPME, diethyl ether, and DME to obtain a purified terpenoid amino alcohol derivative.

In at least one embodiment of the present disclosure, the crude terpenoid amino alcohol derivative may be in a toluene solution.

In at least one embodiment of the present disclosure, the organic salt obtained by the acid/base crystallization process is represented by formula V" below:

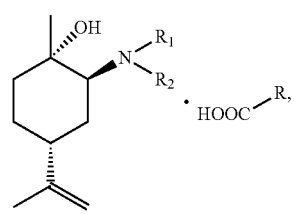

V"

wherein R is a substituted or unsubstituted C1-C6 alkyl.

In at least one embodiment of the present disclosure, the R group shown in formula V" may be, but not limited to, methyl, ethyl, n-propyl, n-butyl, isobutyl, sec-butyl, an alkyl optionally substituted with hydroxyl, carboxyl, halogen, cyano, C1-C4 alkoxy, C1-C4 alkyl-carbonyl, or C1-C4 alkoxy-carbonyl.

In at least one embodiment of the present disclosure, the organic salt obtained by the acid/base crystallization process is represented by formula VI or VII below:

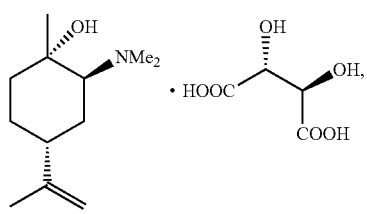

VI

-continued

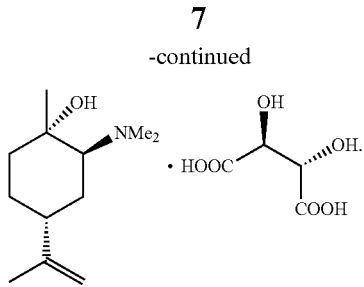

VII

In at least one embodiment of the present disclosure, the acid/base crystallization process is performed by mixing the crude terpenoid amino alcohol derivative as a base or a toluene solution containing the crude terpenoid amino alcohol derivative with an organic acid in an organic solvent or an organic/aqueous solution.

In at least one embodiment of the present disclosure, the acid/base crystallization process is performed by adding the crude terpenoid amino alcohol derivative into a formulation comprises L-tartaric acid, acetone, and water, and the organic salt represented by formula VI can thus be obtained.

In at least one embodiment of the present disclosure, the acid/base crystallization process is performed at a low temperature. In some embodiments of the present disclosure, the low temperature may be in a range of from −5° C. to 30° C.; for example, the temperature may be about 0° C., about 5° C., about 10° C., about 15° C., about 20° C., or about 25° C.

The present disclosure is also directed to a method of preparing p-mentha-2,8-diene-1-ol from the purified terpenoid amino alcohol derivative.

In at least one embodiment of the present disclosure, the preparation method comprises: oxidizing the purified terpenoid amino alcohol derivative with $H_2O_2$ to form a reaction mixture; and performing a Cope elimination of the reaction mixture to obtain p-mentha-2,8-diene-1-ol.

In at least one embodiment of the present disclosure, the oxidization is performed at a temperature ranging from 50° C. to 70° C.; for example, the temperature may be between about 50° C. and about 60° C., between about 55° C. and about 70° C., or between about 55° C. and about 60° C.

In at least one embodiment of the present disclosure, the preparation method further comprises cooling the reaction mixture to about 20° C. to about 30° C., and quenching the oxidization with $Na_2SO_3$ and $H_2O$. In some embodiments of the present disclosure, the preparation method may further comprise distilling the reaction mixture to obtain a solid p-mentha-2,8-diene-1-ol after the Cope elimination.

In at least one embodiment of the present disclosure, the terpenoid amino alcohol derivative used in the method of the present disclosure may be provided by the step of reacting a mixture comprising intermediates represented by following formulas I and II with dimethylamine in an alcohol:

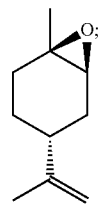

I

-continued

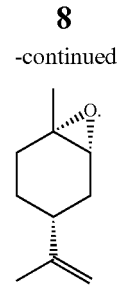

II

In at least one embodiment of the present disclosure, the above reaction of the mixture may be performed at a temperature ranging from 50° C. to 60° C., and the alcohol may be methanol (MeOH).

In at least one embodiment of the present disclosure, the mixture comprising intermediates represented by formulas I and II is provided by performing an epoxidation of limonene.

In some embodiments, the epoxidation of limonene is performed with an oxidant at a low temperature. In at least one embodiment of the present disclosure, the oxidant is peracetic acid in acetic acid (HOAc), and the low temperature is at around 0° C. In some embodiments, meta-chloroperoxybenzoic acid (mCPBA) may be selected as an oxidant in $CHCl_3$ for epoxide preparation.

In the present disclosure, the terpenoid amino alcohol derivative of formula V is obtained by directly reacting epoxide intermediates of formulas I and II with dimethylamine. Therefore, the terpenoid amino alcohol derivative of formula V can be easily purified with L-tartaric acid and D-tartaric acid as 1:1 ratio to form stable organic salts, which is shown as formulas VI and VII.

Further, salt break can be conducted with NaOH in toluene to obtain high purity (e.g., about 97% purity) of formula V without using an energy-costly distillation process or an unpurified reactant for an ongoing process. It is thus useful for improving efficiency of the preparation process of p-mentha-2,8-diene-1-ol.

Many examples have been used to illustrate the present disclosure. The examples below should not be taken as a limit to the scope of the present disclosure.

EXAMPLE

Example 1: Preparation of Intermediates of Formula I and Formula II $H_2O$ (223 kg), $Na_2WO_4 \cdot H_2O$ (10 kg), cetyltrimethylammonium bromide (CTAB, 10.4 kg), 45% $NaOH_{(aq)}$ (2.9 kg), $H_2SO_4$ (3.2 kg), $H_3PO_4$ (5.2 kg), limonene (650 kg), and dichloromethane (1625 kg) were mixed and stirred in a tank, and then 50% $H_2O_2$ (372 kg) was added into the reaction mixture. After the reaction completed, $Na_2S_2O_3$ (82 kg) and $H_2O$ (390 kg) were added for quenching, resulting in phase separation. The organic phase was concentrated under reduced pressure to collect the mixture (711 kg) comprising crude intermediates of formulas I and II shown below for the next step without further purification.

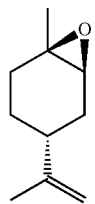

I

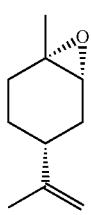

II

Example 2: Preparation and Purification of Formula V

The mixture of crude intermediates of formulas I and II was mixed with aqueous dimethylamine (520 kg) and MeOH (650 kg) in a reaction tank, and then heated to inner temperature around 50° C. to 60° C. for 24 hours. Subsequently, the reaction mixture was concentrated, and toluene (195 kg) and H₂O (390 kg) were added for extraction. The aqueous phase was extracted with another toluene (195 kg), followed by combination of two organic phases. Further, residues (i.e., the crude compound of formula V) were collected after the organic phase concentration for further reaction.

L-tartaric acid (260 kg), H₂O (260 kg), and acetone (1,500 kg) were formulated in a reaction tank, and then the crude compound of formula V was added, wherein the ratio of L-tartaric acid to the crude compound of formula V was 1:1. Afterward, acetone and H₂O were added to obtain the solid organic salt of formula VI (471 kg). The powder x-ray diffraction pattern of the organic salt of formula VI was shown in FIG. 1.

Figure 2:
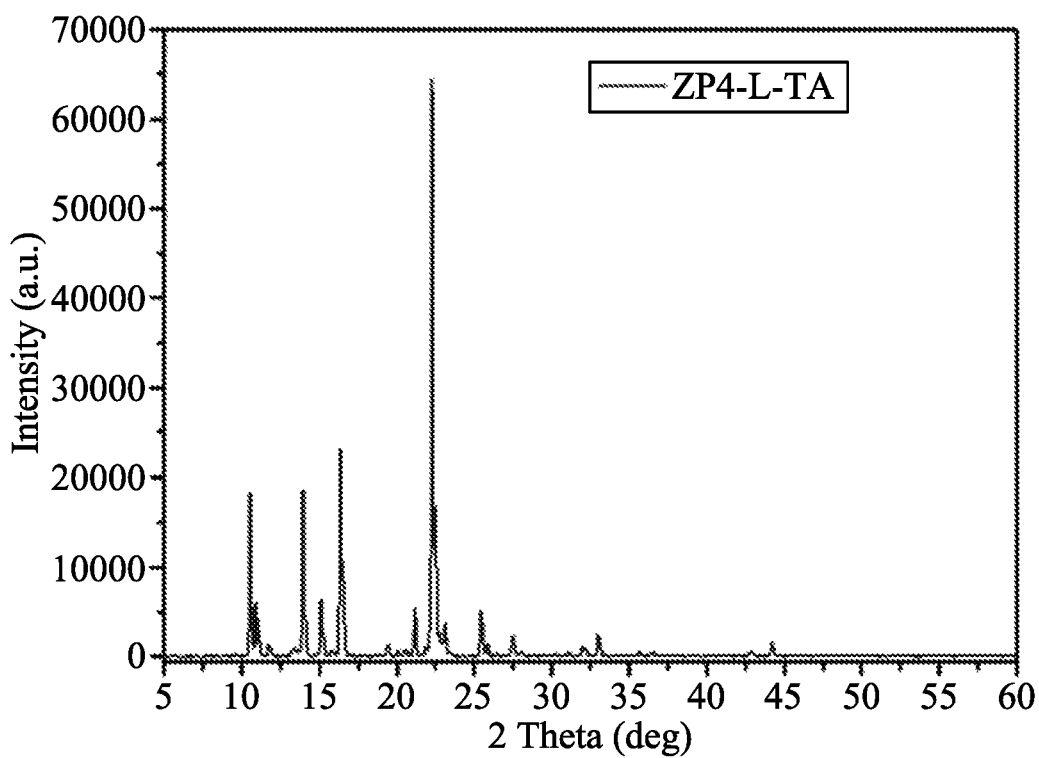
FIG. 2 illustrates the powder x-ray diffraction pattern of an organic salt represented by formula VII.

Alternatively, L-tartaric acid (1 g), H₂O (1 g), and acetone (5.5 g) were formulated in a reaction flask, and then the crude compound of formula V was added, wherein the ratio of L-tartaric acid to the crude compound of formula V was 1:1. Afterward, acetone and H₂O were added to obtain the solid organic salt of formula VII (3 g). The powder x-ray diffraction pattern of the organic salt of formula VII was shown in FIG. 2.

Subsequently, the organic salt of formula VI (471 kg), H₂O (825 kg), 45% NaOH (223 kg) and toluene were mixed and stirred for 1 hour, resulting in phase separation. The organic and aqueous phases were re-extracted by H₂O (130 kg) and toluene (130 kg). Further, the organic phases (520 kg) were combined and concentrated, followed by striping with isopropyl alcohol (IPA) (130 kg) to obtain 97% purity of 260 kg residue 1 (i.e., the purified compound of formula V).

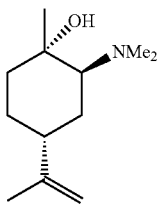

V

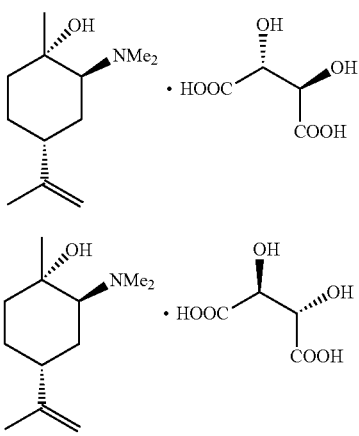

VI

VII

Example 3: Preparation of (+)-p-mentha-2,8-diene-1-ol

Oxidation reaction of the residue 1 (260 kg) obtained by Example 2 was conducted with H₂O₂ (293 kg) in IPA (189 kg) around 60° C. Afterward, the reaction mixture was cooled to about 25° C., and the reaction was quenched with Na₂SO₃ (50 kg) and H₂O (150 kg). By filtration and distillation, 320 kg residue was acquired. Subsequently, (+)-p-mentha-2,8-diene-1-ol (110 kg) was obtained after Cope elimination and purified by distillation.

While some of the embodiments of the present disclosure have been described in detail above, it is, however, possible for those of ordinary skill in the art to make various modifications and changes to the embodiments shown without substantially departing from the teaching and advantages of the present disclosure. Such modifications and changes are encompassed in the scope of the present disclosure as set forth in the appended claims.

What is claimed is:
1. A method of purifying a terpenoid amino alcohol derivative represented by formula V', comprising:
providing a crude terpenoid amino alcohol derivative represented by formula V' below:

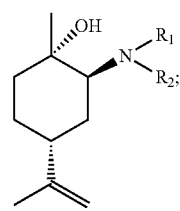

V' performing an acid/base crystallization process of the crude terpenoid amino alcohol derivative represented by formula V' to obtain an organic salt represented by formula V''' below:

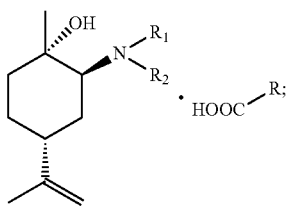

and
reacting the organic salt represented by formula V''' with at least one solvent selected from NaOH, toluene, cyclopentyl methyl ether, diethyl ether, and dimethoxyethane to obtain a purified terpenoid amino alcohol derivative represented by formula V',
wherein R, $R_1$, and $R_2$ are independently a substituted or unsubstituted C1-C6 alkyl.

2. The method of claim 1, wherein the terpenoid amino alcohol derivative is represented by formula V below:

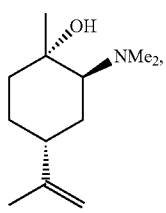

and the organic salt is represented by formula VI or VII below:

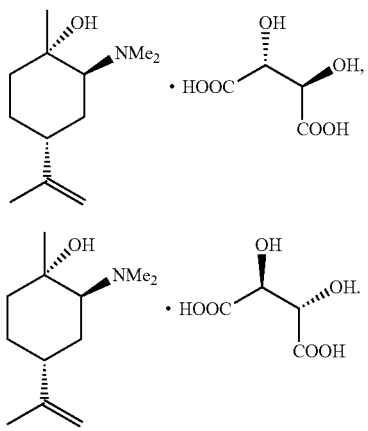

3. The method of claim 1, wherein the acid/base crystallization process is performed by mixing the crude terpenoid amino alcohol derivative represented by formula V' as a base with an organic acid in an organic solvent or an organic/aqueous solution.

4. The method of claim 3, wherein the organic acid is L-tartaric acid, D-tartaric acid, acetic acid, citric acid, camphorsulfonic acid, mandelic acid, (+)-di-tert-butyl tartaric acid, (+)-diethyl tartaric acid, methanesulfonic acid, or a combination thereof.

5. The method of claim 3, wherein a ratio of the organic acid to the base in the mixture is 1:1 to 1:3.

6. The method of claim 5, wherein the ratio of the organic acid to the base in the mixture is 1:1.

7. The method of claim 3, wherein the organic solvent is isopropyl alcohol.

8. The method of claim 3, wherein the organic/aqueous solution is an acetone/$H_2O$ solution.

9. The method of claim 1, wherein the acid/base crystallization process is performed at a temperature ranging from −5° C. to 30° C.

10. The method of claim 9, wherein the temperature is in a range from 5° C. to 15° C.

11. The method of claim 1, further comprising stripping the purified terpenoid amino alcohol derivative represented by formula V' with isopropyl alcohol or an acetone/$H_2O$ solution.

12. A method of preparing p-mentha-2,8-diene-1-ol, comprising:
purifying the terpenoid amino alcohol derivative represented by formula V' below according to the method of claim 1:

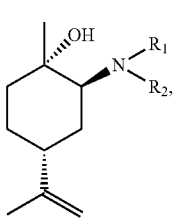

wherein $R_1$ and $R_2$ are independently a substituted or unsubstituted C1-C6 alkyl;
oxidizing the purified terpenoid amino alcohol derivative represented by formula V' with $H_2O_2$ to form a reaction mixture; and
performing a Cope elimination of the reaction mixture to obtain p-mentha-2,8-diene-1-ol.

13. The method of claim 12, wherein the oxidization is performed in isopropyl alcohol or an acetone/$H_2O$ solution.

14. The method of claim 12, wherein the oxidization is performed at a temperature ranging from 50° C. to 70° C.

15. The method of claim 12, further comprising quenching the oxidization with $Na_2SO_3$ and $H_2O$.

16. The method of claim 12, further comprising distilling the reaction mixture after the Cope elimination.

17. The method of claim 12, further comprising providing a mixture comprising intermediates represented by formulas I and II below:

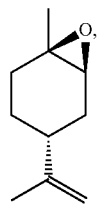

-continued

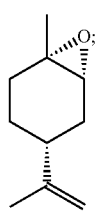
II and
reacting the mixture with dimethylamine in an alcohol to obtain the terpenoid amino alcohol derivative represented by formula V'.

18. The method of claim 17, wherein the reaction of the mixture is performed at a temperature ranging from 50° C. to 60° C.

19. The method of claim 17, wherein the alcohol is methanol.

20. The method of claim 17, further comprising performing an epoxidation of limonene to provide the mixture.

* * * * *